(12) United States Patent
Cagnan et al.

(10) Patent No.: US 8,831,307 B2
(45) Date of Patent: Sep. 9, 2014

(54) VISUALIZING SURGICAL TRAJECTORIES

(75) Inventors: Hayriye Cagnan, Eindhoven (NL);
Hubert Cecile Francois Martens, Eindhoven (NL); Kevin Thomas Dolan, Oxford (GB)

(73) Assignee: Koninklijke Philips N.V., Eindhoven (NL)

(*) Notice: Subject to any disclaimer, the term of this patent is extended or adjusted under 35 U.S.C. 154(b) by 36 days.

(21) Appl. No.: 13/378,094

(22) PCT Filed: Jun. 21, 2010

(86) PCT No.: PCT/IB2010/052785
§ 371 (c)(1),
(2), (4) Date: Dec. 14, 2011

(87) PCT Pub. No.: WO2011/001322
PCT Pub. Date: Jan. 6, 2011

(65) Prior Publication Data
US 2012/0099770 A1  Apr. 26, 2012

(30) Foreign Application Priority Data
Jun. 29, 2009  (EP) .................................. 09163970

(51) Int. Cl.
*G06K 9/00* (2006.01)
*A61B 19/00* (2006.01)

(52) U.S. Cl.
CPC .......... *A61B 19/50* (2013.01); *A61B 2019/524* (2013.01); *A61B 2019/5289* (2013.01); *A61B 19/5244* (2013.01); *A61B 2019/505* (2013.01); *A61B 2019/507* (2013.01)
USPC ........................................................ 382/128

(58) Field of Classification Search
USPC ........................................................ 382/128
See application file for complete search history.

(56) References Cited

U.S. PATENT DOCUMENTS

| | | | |
|---|---|---|---|
| 5,638,819 A * | 6/1997 | Manwaring et al. | 600/424 |
| 2001/0034530 A1 | 10/2001 | Malackowski et al. | |
| 2004/0087852 A1 * | 5/2004 | Chen et al. | 600/407 |
| 2008/0071292 A1 | 3/2008 | Rich | |
| 2008/0097187 A1 | 4/2008 | Gielen et al. | |
| 2008/0183188 A1 | 7/2008 | Carls et al. | |
| 2011/0245660 A1 * | 10/2011 | Miyamoto | 600/424 |

OTHER PUBLICATIONS (L. Joskowicz, "Image-guided System with Miniature Robot for Precise Positioning and Targeting in Keyhole Neurosurgery", Computer Aided Surgery, Jul. 2006).*

Guo et al., "Development and Application of Functional Databases for Planning Deep-Brain Neurosurgical Procedures", Springer-Verlag Berlin Heidelberg 2005, pp. 835-842.

* cited by examiner

*Primary Examiner* — Stephen R Koziol
*Assistant Examiner* — Totam Le

(57) ABSTRACT

A method is provided for visualizing a surgical trajectory (32, 101, 42, 46, 47). The method comprises steps of receiving (71) 3D imaging information (31) of a region to undergo surgery and combining (72) the received 3D imaging information (31) with data from a digitized anatomical atlas. As a result, a combined map of the region to undergo surgery is obtained. The combined map comprises expected positions of anatomical structures (102, 103, 104) in the region to undergo surgery. The method further comprises steps of receiving (73) the surgical trajectory (32, 101, 42, 46, 47) for the surgery, determining (74) positions of intersections (43, 44) of the surgical trajectory (32, 101, 42, 46, 47) with the anatomical structures (102, 103, 104) and providing (75) the positions of the intersections (43, 44) in a coordinate system aligned with the surgical trajectory (32, 101, 42, 46, 47).

17 Claims, 9 Drawing Sheets

VISUALIZING SURGICAL TRAJECTORIES

FIELD OF THE INVENTION

This invention relates to a method for visualizing a surgical trajectory. The method combines 3D imaging information with a digitized anatomic model for segmenting anatomical structures in the 3D imaging information. A planned surgical trajectory is projected onto the combined images for visualizing the surgical trajectory.

This invention further relates to a system and a computer program product for performing said method.

BACKGROUND OF THE INVENTION

Such a method is, e.g., known from Guo et al., 'Development and Application of Functional Databases for Planning Deep-Brain Neurosurgical Procedures'. From Guo et al. it is known to fuse pre-operative MR images of individual patients with digitized anatomical atlases. From the MR images alone it is very difficult or even impossible to visually distinguish small different neurological structures such as the subthalamic nucleus (STN) which is often targeted during deep brain stimulation procedures. When using additional information from anatomic atlases and/or probabilistic functional atlases, it is possible to enhance the accuracy and precision for localizing surgical targets from this pre-operative surgical planning. In Guo et al. probabilistic functional atlases based on additional standardized electrophysiological information available prior to surgery are used to assist the surgical target determination and to provide anatomical labeling to the 3D image data. The fused images and the standardized electrophysiological information together serve to enable display of the position of a probe needle along a real or simulated surgical trajectory. The position of the probe needle is displayed in a 3D image volume and in 2D slices of a patient.

However, registration of the atlas to pre-operative MR images has limited precision due to registration errors inherent to any registration method. Image-processing such as segmentation may be utilized to further improve the anatomic labeling. However, also this technique has inherent limited accuracies. Further, during surgery an implanted probe may unintentionally deviate from a planned trajectory (e.g. due to an imperfection such as a slight bending of the probe) or the anatomy may slightly shift due to the surgical procedure itself (e.g. the implantation of the probe in the tissue generates a small force field that pushes aside the tissue; loss of cerebrospinal fluid during the surgery may lead to pressure-changes in the tissue resulting in larger deformations referred to as 'brain-shift'). Precision implantation of a probe in a small target therefore usually requires intra-operative measurements (e.g. electrophysiological measurements) to exactly pinpoint the target and to correct for errors due to inaccuracies in the pre-operative planning or due to anatomic shifts during surgery or due to (unintended) deviations of the probe from the planned trajectory. Correct interpretation of such intra-operative measurements is crucial to accurate target localization but may be a very difficult analysis to perform due to the complexity of the data and the amount of information needed to be processed by experts when performing this analysis.

It is a problem of the method described in Guo et al. that the resulting data does not provide sufficiently clear and unambiguous information for the surgeon, which information could help the physician with recognizing the types of neurological structures to expect and with localizing a surgical target along the planned and traversed surgical paths.

OBJECT OF THE INVENTION

It is an object of the invention to provide a clearer way of displaying sufficiently clear information for the surgeon in order to know what type of neurological structures to expect along the planned and traversed surgical path.

SUMMARY OF THE INVENTION

According to a first aspect of the invention, this object is achieved by providing a method of visualizing a surgical trajectory, the method comprising, receiving 3D imaging information of a region to undergo surgery, combining the received 3D imaging information with data from an anatomic model repository, e.g. a digitized anatomical atlas, to obtain a combined map of the region to undergo surgery, the combined map comprising expected positions of anatomical structures in the region to undergo surgery, receiving the surgical trajectory for the surgery, determining positions of intersections of the surgical trajectory with the anatomical structures and providing the positions of the intersections in a coordinate system aligned with the surgical trajectory.

As a result of this method, the user receives a clear overview of what anatomical structures are to be expected at what position along the surgical trajectory. In fact, the method according to the invention maps the 3D anatomical information onto the surgical path. With the method according to the invention, the user knows what structures are to be expected at what position along a planned or navigated surgical path. Therefore it is easier to evade critical structures, localize the surgical target or, e.g., release a certain drug at a particular anatomical structure.

The method according to the invention combines (i) 3D medical imaging information with (ii) an anatomical model repository for segmenting anatomical structures in the 3D medical imaging information and (iii) local measurements indicative of anatomy or tissue-type from a surgical probe obtained during the surgical intervention. The model repository is combined with the 3D imaging information to provide 3D anatomical labeling of the imaging information (e.g. by registering a digital anatomic atlas to the MRI). At least one planned surgical trajectory towards at least one surgical target is combined with the anatomically labeled 3D images and the cross-section of the trajectory with the anatomically labeled 3D imaging information is projected as anatomical labeling onto the surgical trajectory.

Optionally, the medical imaging data and associated anatomical labeling may be updated intra-operatively by perioperative imaging e.g. using flat-panel 3D x-ray system, interventional MRI or 3D ultrasound. Local measurements using at least one surgical probe may be made along the planned surgical trajectory to intra-operatively support the identification of the anatomy type at the probe's measurement location(s). Data extracted from the local measurements are co-visualized with the labeled surgical trajectory to aid their interpretation and to support the intra-operative accurate localization of the surgical target. Data extracted from the local measurements may further be combined with the labeled surgical trajectory for computer processing (e.g. using feature clustering analysis algorithms) to extract characteristic features indicative of certain anatomy that may be presented to the users in order to support target localization.

In a preferred embodiment, the combined map comprises a statistical map of the region to undergo surgery, the statistical map comprising probabilities of a presence of the anatomical structures at positions in the region. In such a statistical map, transitions from one anatomical structure to another are not sharp, but come gradually. The intersections thus do not represent single points where one structure lies adjacent to another one. Instead, the intersections are sections of the surgical path wherein a probability of a first structure gradually decreases while the probability of at least one other structure gradually increases. For example, at a certain position along the surgical path there may be a 30% probability of being at a first structure and a 70% probability of being at a second structure. At some positions even more than two different anatomical structures may have a significant probability. It is to be noted that a method using sharp intersections only uses probabilities of 0% and 100%.

For a clear indication of what structures are to be expected at what position in the surgical trajectory, the positions of the intersections may be provided as a distance between the intersections and a target of the surgical trajectory. This makes it possible for the user to see how close to the target area a specific anatomical structure may be expected. The surgical trajectory may be a planned or a navigated trajectory. While planning a trajectory, the method assists in finding a relatively safe and easily accessible route to the target. When navigating a trajectory using a surgical tool, the method according to the invention may help the user to see at what type of anatomical structure he is currently working and, possibly, what types of structures may be expected when following the path further towards a target structure.

In a practical embodiment of the method according to the invention, the surgical tool is an electrophysiological probe and the method further comprises a step of receiving electrophysiological signals from the probe, a step of extracting features from the received electrophysiological signals, a step of relating the extracted features to positions in the coordinate system, and a step of visualizing the extracted features in combination with the related positions in the coordinate system.

In an embodiment, CT or CT-like 3D image data of a region around the spine is used. Using segmentation and anatomic modeling the 3D image is anatomically labeled and a surgical trajectory is planned. A surgical probe with integrated fiber for optical reflectance measurement is used for local anatomic mapping at probe's tip ('photonic needle'). The 3D image information and associated anatomic labeling is updated by perioperative 3D x-ray using a flat panel rotational x-ray system. Optical spectra are acquired at different probe positions. Optical spectra are visualized together with a map that visualizes proximity and directionality of certain anatomic labeling with respect to the surgical probe's tip based on the navigated trajectory of the surgical probe's tip in the 3D (anatomically labeled) image.

These and other aspects of the invention are apparent from and will be elucidated with reference to the embodiments described hereinafter.

DETAILED DESCRIPTION OF THE INVENTION

In the following, the invention will be described by an exemplary embodiment related to neurosurgery using electrophysiological probes. The invention is however not limited to use with a neuro-EP system. Other surgical interventions where knowledge about anatomic information along a surgical trajectory (planned and/or navigated) is useful for clinical and/or diagnostic purposes may benefit as well from this invention. The invention may, e.g., be suitable for optical-needle guided interventions.

Figure 1:
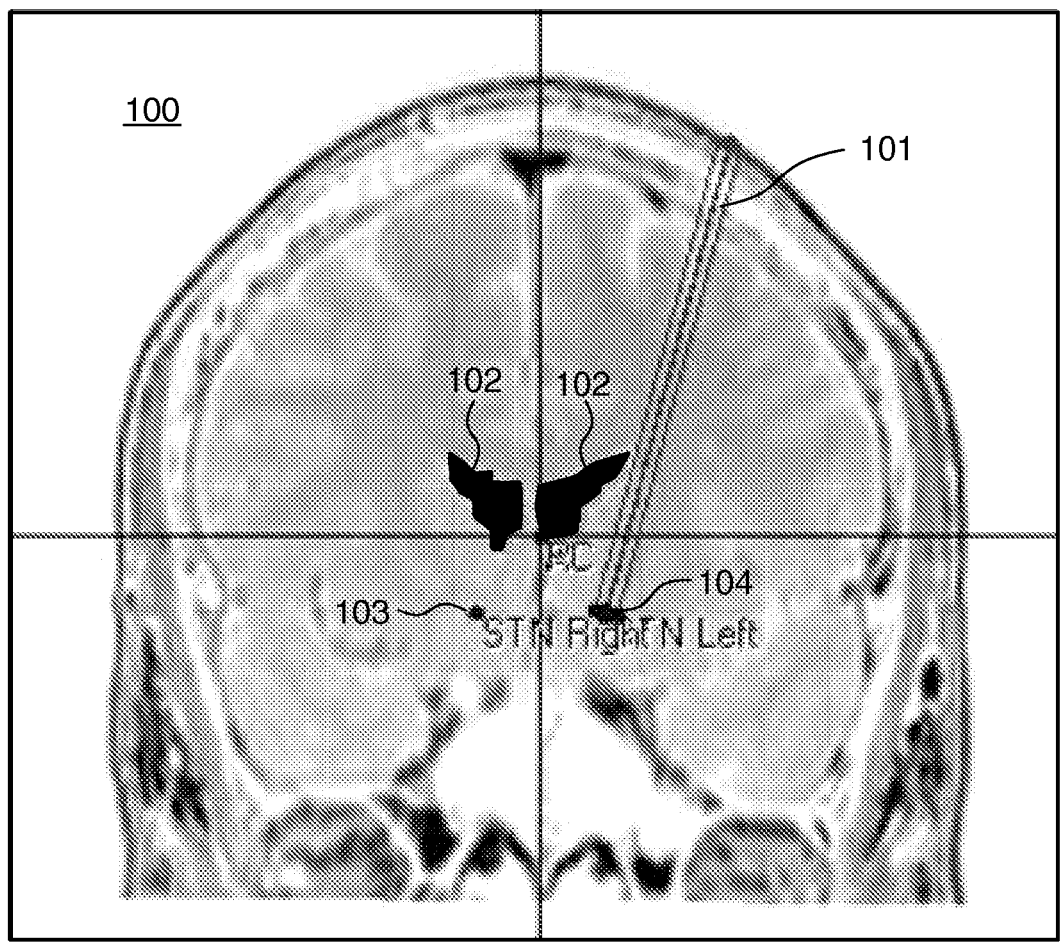
FIG. 1 shows an image comprising data from an MRI, an atlas and a surgical trajectory.

FIG. 1 shows an image 100 comprising data from an MRI, an atlas and three surgical trajectories 101. It is known to use such an image 100 for pre-operative planning of a surgical trajectory In this image atlas information is used for indicating specific structures 102, 103, 104 in the region of the brain which is shown in the MRI image. The image 100 shows an MRI image of a cross section of a human brain. The surgical trajectory 101 runs through the brain tissue towards the target 104 of the planned surgery. In this example, the target 104 of the surgery is a specific part of the subthalamic nucleus (STN) 104. In this example, the trajectory 101 is chosen such that another structure 102 will not be touched or damaged by the surgical tool used for the surgery. It is, e.g., very important to avoid damaging major blood vessels or ventricles.

Figure 2:
FIG. 2 shows an example of an output of an electrophysiological recording.

The image 100 of FIG. 1 helps with planning the surgical operation. While performing the surgery, it is known to use electrophysiological (EP) recordings. FIG. 2 shows an example of an output 200 of an EP recording. Such a neuro-EP recording is commonly performed using so-called microelectrode needles; these are needles carrying a tiny electrode (approximately 10 micron diameter) at the tip and that can be used to pick up the electrical signals ('spikes') from individual brain cells (neurons) near the electrode tip. In a typical procedure, the neurophysiologist will investigate the recordings at multiple positions (up to 100 positions; each recording being typically 10-20 s of data). Usually such recordings are performed at incremental depth positions, with typical step sizes of 0.5 mm, i.e. well below the resolution available in clinical MRI systems. Based on a comparison of the statistical characteristics of the various recordings (e.g. spike-timing characteristics such as burstiness and average firing-rate, noise amplitude, etc.) the neurophysiologist has to translate the measured data to the functional properties of the investigated locations, i.e. assign a functional anatomy to the recorded positions. As is clear from FIG. 2, the analysis of EP-recordings is complex and requires a lot of expertise, especially when it needs to be performed under time pressure. Therefore, according to the invention, a system is provided for visualizing a surgical trajectory.

Figure 3:
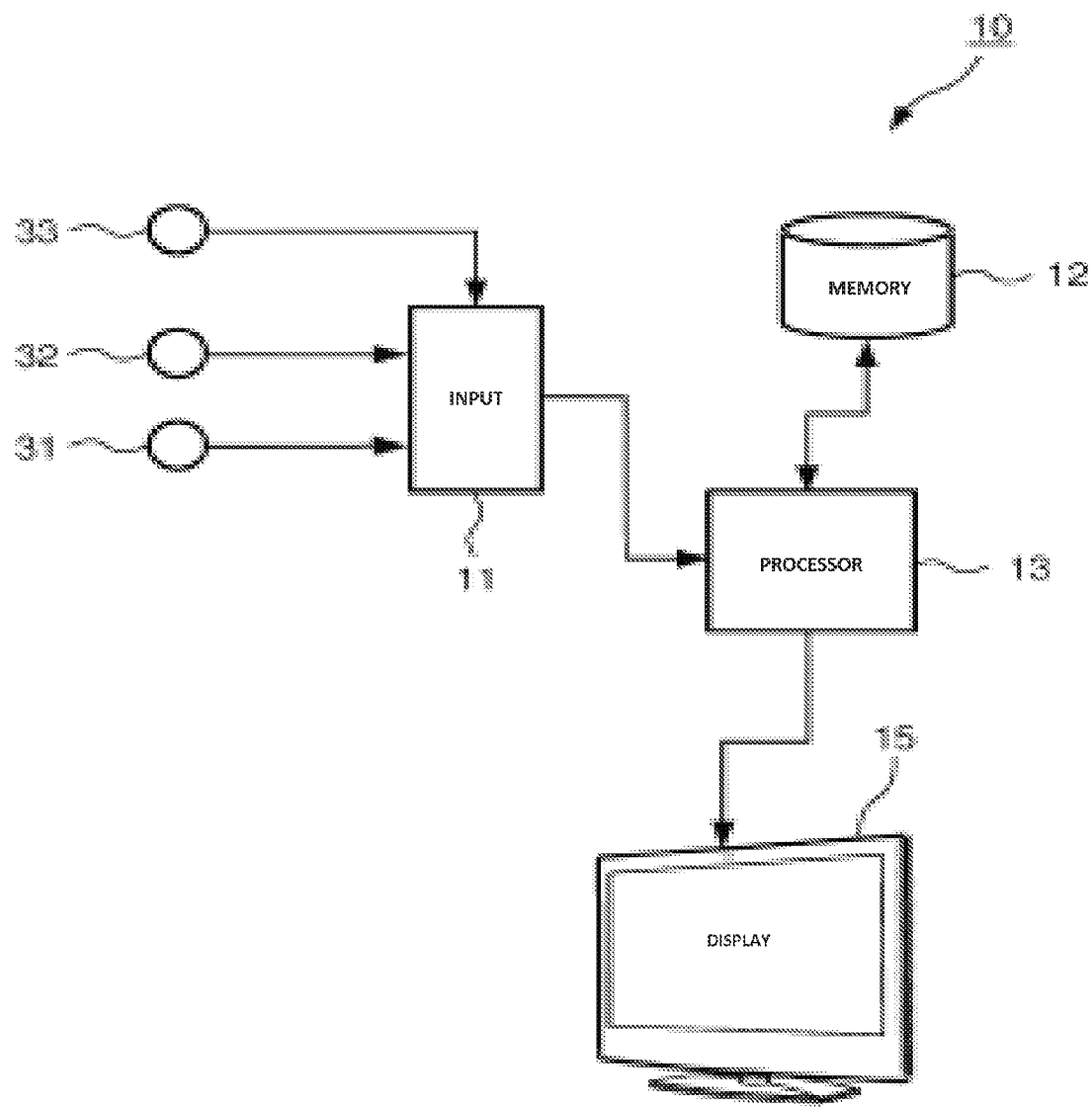
FIG. 3 shows a block diagram of a system according to the invention.

FIG. 3 shows a block diagram of a system 10 according to the invention. The system 10 comprises an input 11 for receiving 3D imaging information 31 of a region to undergo surgery. The 3D image 31 information may come from, e.g., an MRI or CT scanner. The input 11 is also provided for receiving trajectory information 32 defining a planned or navigated surgical trajectory. Optionally, e.g. if the system 10 is used for visualizing real time trajectory information during a surgical operation, the input 11 is also provided for receiving EP-data 33 from an EP recording system. A processor 13 is provided for processing the incoming data 31, 32, 33. The processing of the data comprises several steps, of which some are required and some are optional. First, the received 3D image information 31 is combined with data from a digitized anatomical atlas to obtain a combined map of the region to undergo the surgery. The anatomical atlas data may come from a database stored on a memory device 12 which is part of the system 10. Alternatively, the system 10 is coupled to such a database via a closed network or wide area network, such as the Internet, for receiving atlas data there from. In this embodiment, a so-called anatomical atlas is used to obtain anatomic data of the relevant areas. However, this anatomic data can also be provided in another way, e.g. by a suitable imaging modality. An example is intensity value segmentation of CT images, coupled to different types of tissue (bone, blood, etc.), to obtain the anatomic data. In general, the anatomic data may be obtained from an anatomic model stored in a suitable way.

The combined map comprises expected positions of anatomical structures in the region to undergo surgery. The combined map is created using image recognition techniques for finding transitions between structures in the 3D image information and by comparing the 3D images to information from the anatomical atlas. The combined map may, e.g., be an image or a list of data points describing expected positions of important anatomical structures. The map may look like the image 100 shown in FIG. 1. When the combined map is available, the processor 13 uses the received surgical trajectory data 32 to determine positions of intersections of the surgical trajectory with the anatomical structures. When the positions of these intersections are known, it is also known what anatomical structure lies on the surgical trajectory. This makes it possible to plan and follow a trajectory which does not harm critical structures, such as large blood vessels.

The positions of these intersections are provided in a coordinate system aligned with the surgical trajectory. Such a coordinate system helps in providing an intuitive overview of the anatomical structures which are to be expected along the trajectory. For example, the positions of the intersections may be provided as a distance from the start or target point of the trajectory. The distance is preferably measured along the trajectory. When the positions of the intersections are known, the information may be visualized by, e.g., displaying the trajectory or a graphical representation of the trajectory on a display 15. With the use of, e.g., text labels, color coding or highlighting the positions of important structures relative to the surgical trajectory is displayed.

Figure 4:
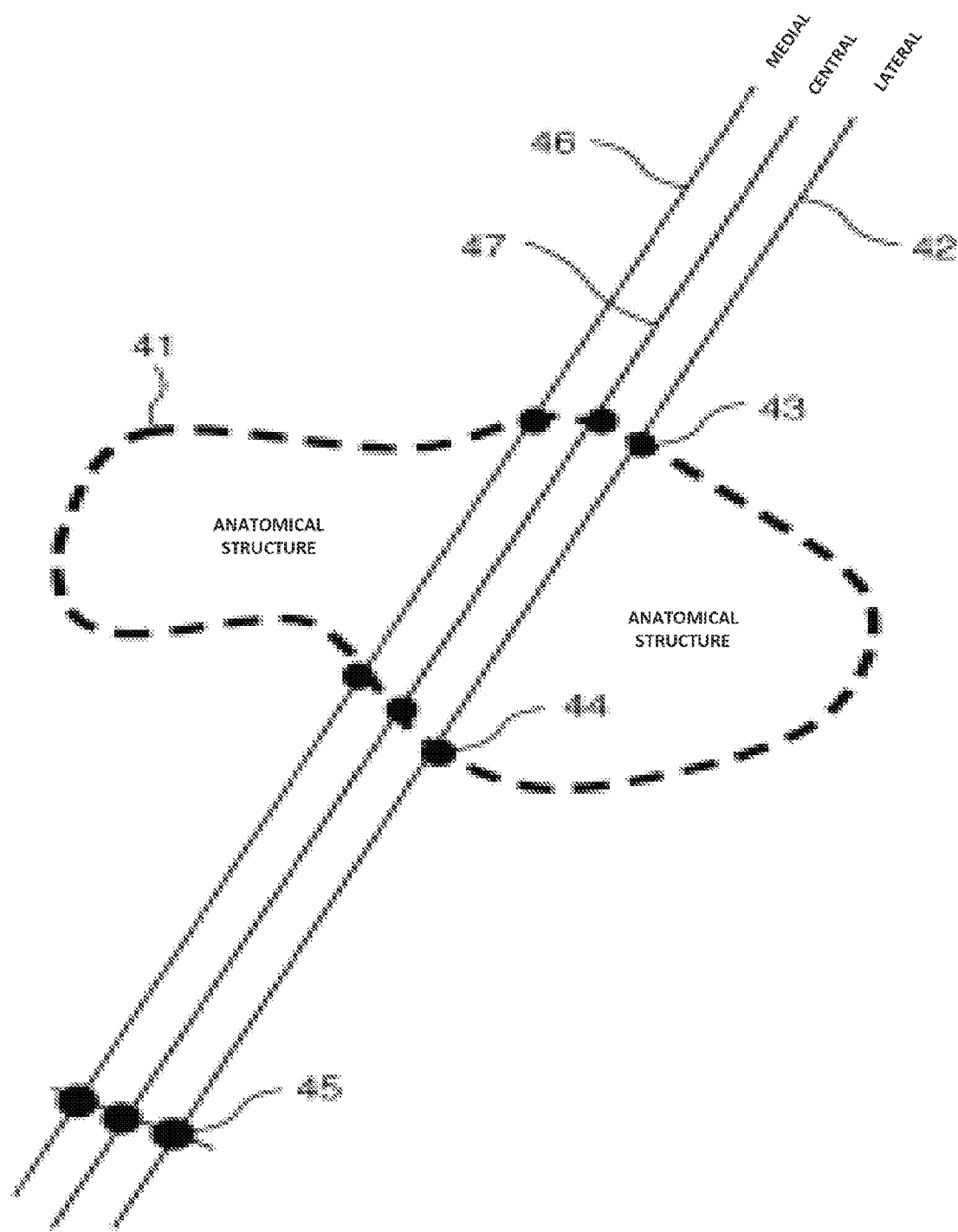
FIG. 4 illustrates the computation of a position of an intersection of an anatomical section and a surgical trajectory.

FIG. 4 illustrates the computation of a position of an intersection 43, 44 of an anatomical section 41 and a surgical trajectory 42. In neurosurgery, often more than one needle is used for the surgical operation. Typically, five micro-recording needles are used, which are called 'central', 'lateral', 'medial', 'anterior' and 'posterior'. Each needle has its own trajectory 42, 46, 47, and its own intersections 43, 44 with anatomical structures 41. In addition, each surgical trajectory will usually end at a slightly different target point 45. The positions of the intersections 43, 44 are thus to be calculated for each needle separately and for each needle said positions 43, 44 are provided in a coordinate system aligned with the respective surgical path 42, 46, 47.

Figure 5:
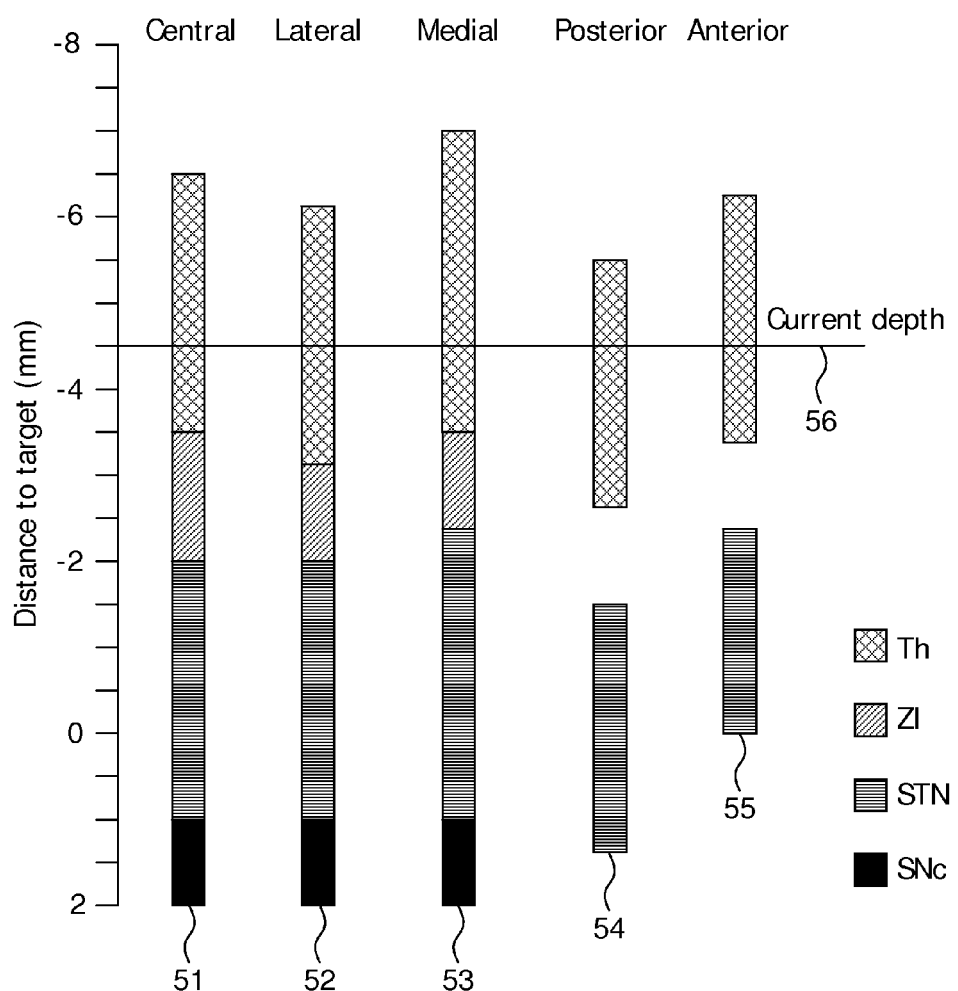
FIGS. 5, 6 and 7 show exemplary visualizations of a surgical trajectory provided by a system according to the invention.
Figure 6:
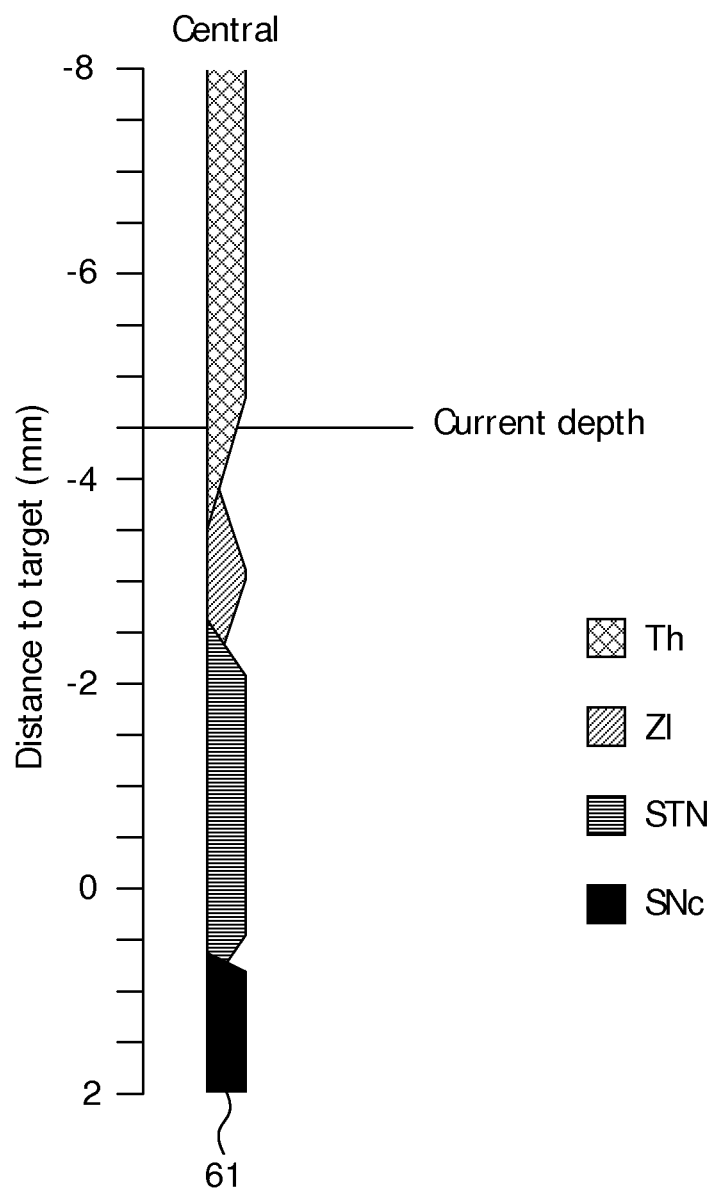
Figure 7:
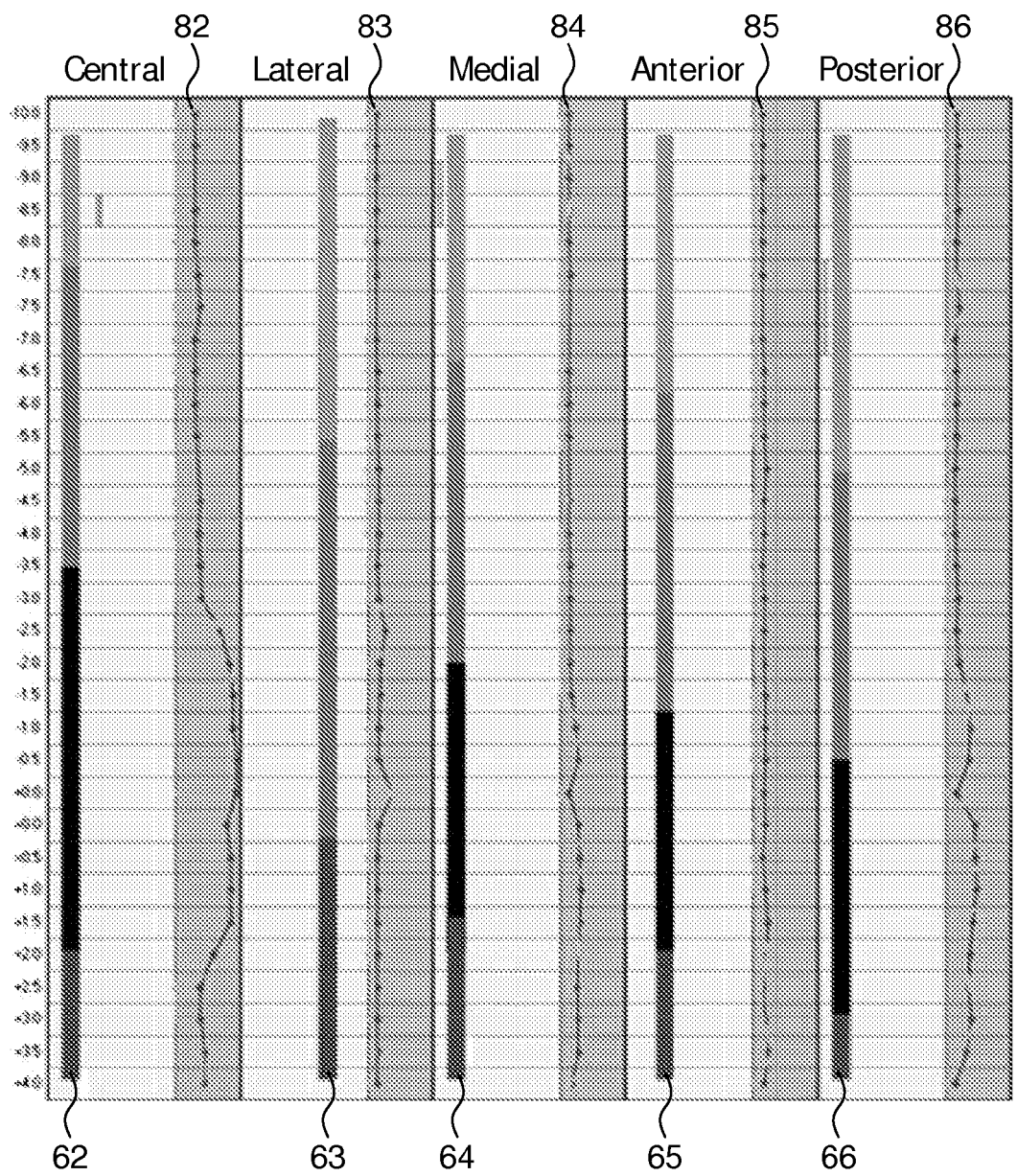

FIGS. 5, 6 and 7 show exemplary visualizations of surgical trajectories provided by a system 10 according to the invention. In FIG. 5, the anatomical structures situated along the planned surgical paths of five EP-needles are visualized. The surgical procedure has the subthalamic nucleus (STN) as a target. At a distance of 0 mm from the target points, all five needles are in the subthalamic nucleus. For the central 51, lateral 52 and medial 53 needle, it is determined that before the subthalamic nucleus, the zona incerta (ZI) and the thalamus (Th) are traversed. The posterior 54 and the anterior 55 needle are also expected to traverse the thalamus (Th). When the needles are inserted into the patient's brain beyond the target points, the substantia nigra pars compacta (SNc) may be entered. As can be seen in FIG. 5, not all needles will reach the same structures at the same distance from the target. The system and method according to the invention make it possible to see for each needle, when it is expected to reach what anatomical structure.

The shaded bar graph sections in FIG. 5 represent expected anatomical structures on a planned surgical path. While performing the surgery, this picture may be used for showing the surgeon what is to be expected and where the needles are currently situated. At a current depth a line 56 is drawn to show where the needles currently are. In FIG. 5 all needles are in the thalamus (Th). In this embodiment, all needles are moved together and have the same distance to their respective target points. Alternatively, the needles are operable separately and each needle has its own corresponding current depth level.

In FIG. 6, the trajectory of only one needle 61 is visualized. In this embodiment, the intersections of the surgical trajectory with the anatomical structures are not shown as a sharp transition from one structure to another. The procedure of combining the 3D images of the region to be subject to surgery with data from the anatomical atlas results in expected positions for the different structures with some margins of error. In particular at positions close to the transition from one tissue type to another, it may not be possible to be completely sure about the type of anatomical structure. Therefore, this embodiment uses a statistical map of the region to undergo surgery. The statistical map comprises probabilities of a presence of an anatomical structure at a certain position. When using such a statistical map for visualizing the surgical path of a needle 61, the results may be like the bar graph in FIG. 6. E.g., at the 'current depth', the needle probably is in the thalamus (Th). When the needle will traverse the path a little bit further, it will arrive at a position where it is not known whether it already is in the zona incerta (ZI) or still in the thalamus (Th).

FIG. 7 shows a visualization of the anatomical structures at five surgical trajectories 62, 63, 64, 65, 66 together with parameter values 82, 83, 84, 85, 86 extracted from intraoperatively obtained neuro-EP data at those same locations. This representation aids the decision process as both anatomical and EP data are available in a simple overview. The neuro-EP data may be derived from one or more probes used for, e.g., localizing a functional target in deep brain stimulation (DBS) therapy. Automated neuro-EP analysis methods are known for extracting certain signal features from the raw data. By relating these extracted features to positions in the coordinate system used for visualizing the anatomy along the (planned or traversed) path, the relevance of the extracted values can more easily be assessed. False negatives and/or false positives which do often occur when extracting features from neuro-EP data are recognized more easily when presenting the extracted features together with the expected anatomical positions corresponding to these extracted features. Instead of extracting features from the neuro-EP data 33, it is possible to visualize the neuro-EP data itself at the corresponding position where they have been recorded.

In an embodiment, CT or CT-like 3D image data of a region around the spine is used. Using segmentation and anatomic modeling the 3D image is anatomically labeled and a surgical trajectory is planned. A surgical probe with integrated fiber for optical reflectance measurement is used for local anatomic mapping at probe's tip (photonic needle'). The 3D image information and associated anatomic labeling is updated by perioperative 3D x-ray using a flat panel rotational x-ray system. Optical spectra are acquired at different probe positions. Optical spectra are visualized together with a map that visualizes proximity and directionality of certain anatomic labeling with respect to the surgical probe's tip based on the navigated trajectory of the surgical probe's tip in the 3D (anatomically labeled) image.

Figure 8A:
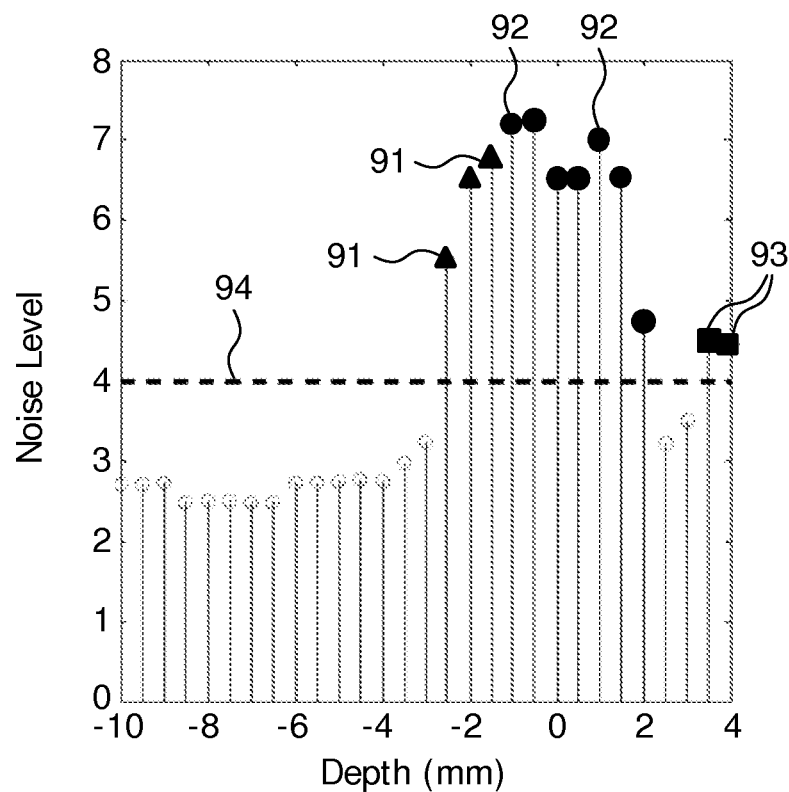
FIGS. 8*a* and 8*b* show further visualizations of neuro-EP parameter values combined with anatomical information about a surgical path.
Figure 8B:
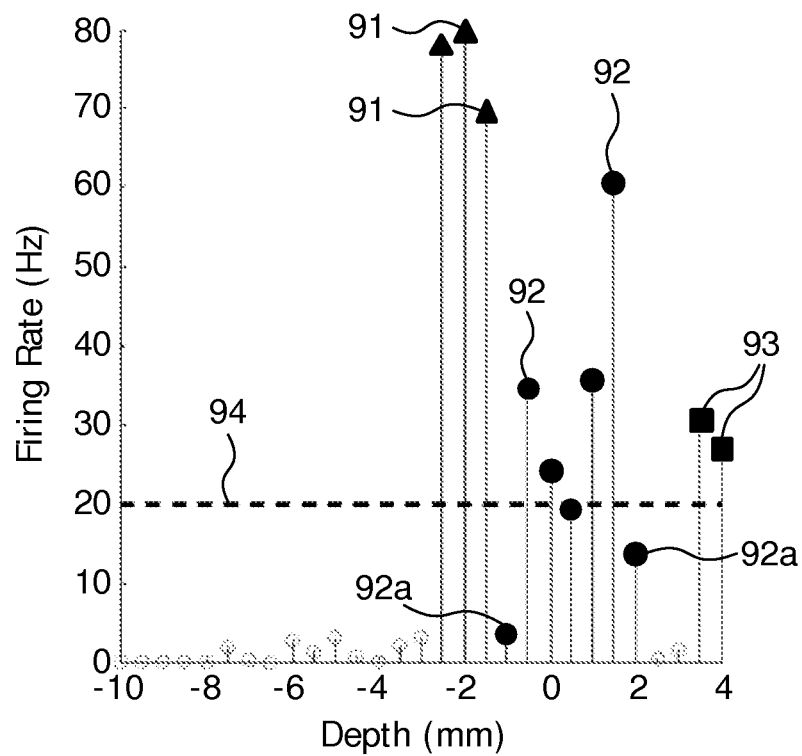

FIGS. 8a and 8b show further visualizations of neuro-EP parameter values combined with anatomical information about a surgical path. FIG. 8a shows a noise level (y-axis) versus a depth along a surgical trajectory (x-axis). The target are of this trajectory is the subthalamic nucleus (STN) which is defined to be at a depth of 0 mm. As can be seen in the figure, the noise level close to the target area is high. A sharp increase is observed upon entering the STN (indicated by triangles 91). Within the STN, noise level stays consistently high (indicated by circles 92) and upon exiting STN, noise level drops steeply. However, the noise level remains above the baseline 94 observed before entering STN, and further increases upon entering the substantia nigra (SN, indicated by squares 93). From FIG. 8a it is clear that noise level alone is not sufficient in distinguishing STN from SN. High noise levels are observed in both anatomical structures. When combining anatomical knowledge and 3D images with neuroEP signals in a way according to the invention, different anatomical structures can be distinguished more easily and reliably.

FIG. 8b shows firing rates (y-axis) versus a depth along the surgical trajectory (x-axis). The entrance to STN is marked with very high firing rates (indicated by triangles 91). Firing Rate decreases within STN (indicated by circles 92) and upon entering SN (indicated by triangles 93) increases again. Therefore, Firing Rate alone is also not sufficient in distinguishing STN from SN. Also, measures such as Firing Rate show high variability due to sensitivity of the measure to proximity of neural units. At some depths along the surgical trajectory and within STN, the firing rate drops below the baseline 94. These positions are indicated by circles 92a. Judging from the firing rate alone, a surgeon may make wrong decisions. When combining anatomical knowledge and 3D images with neuroEP signals in a way according to the invention, different anatomical structures can be distinguished more easily and reliably.

Figure 9:
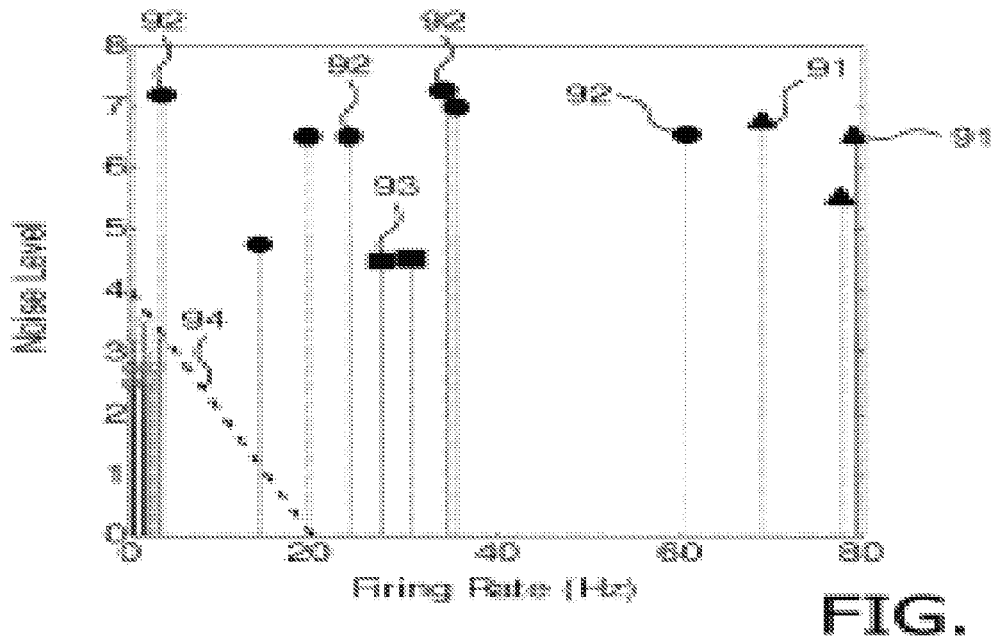
FIG. 9 shows noise level versus firing rate, and FIG. 10 show a flow diagram of a method according to the invention.

In FIG. 9, noise level (y-axis) is plotted versus firing rate (x-axis): In the absence of depth information, the combination of noise level and firing rate clearly distinguishes STN and SN from other regions. All measurements inside STN (triangles 91 and circles 92) and SN (squares 93) are well above the baseline 94. All other measurements are below the baseline 94. However, these measures are not sufficient for distinguishing between STN (circles 92) and SN (triangles 91). With the method and system according to the invention, the depth information is used for distinguishing STN from SN and indicating so in the diagram, e.g., using different shapes or colors for data points at different depths.

Figure 10:
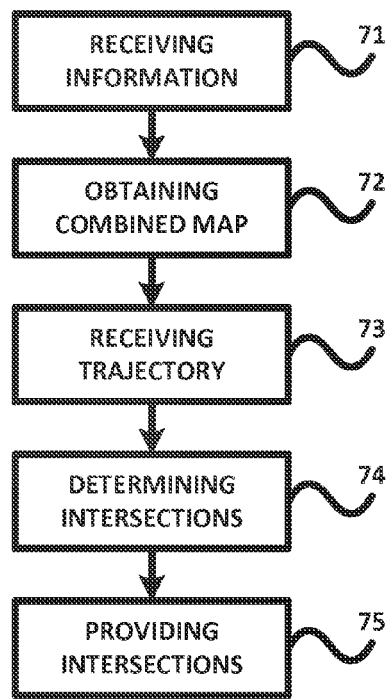

FIG. 10 shows a flow diagram of a method according to the invention. The method starts with an image reception step 71 for receiving 3D imaging information of a region to undergo surgery. The 3D imaging information may, e.g., be obtained from an MRI or CT scanner. In combination step 72 the received 3D imaging information is combined with data from a digitized anatomical atlas to obtain a combined map of the region to undergo surgery. The combined map comprises expected positions of anatomical structures in the region to undergo surgery. In trajectory input step 73 at least one surgical trajectory for the surgery is received. The trajectory may be received as a planned route through the region to undergo the surgery. The received trajectory information may also comprise a current position of a surgical tool. A sequence of actual positions of a surgical tool forms a traversed trajectory. The surgical trajectory received in trajectory input step 73 may either be a planned or an already traversed trajectory. Alternatively, the received trajectory is a combination of a planned and an actually traversed trajectory. Interpolation and extrapolation may be used for forming or adjusting a surgical trajectory.

In intersection calculating step 74, positions of intersections of the at least one surgical trajectory with surfaces of anatomical structures are calculated. These positions are provided as output in output step 75. For easy understanding of the positional data, the positions of the intersections are provided in a coordinate system aligned with the surgical trajectory, such that it is easy to understand what anatomical structures are to be expected at different positions along the surgical trajectory. The provided positions may then be used for visualizing the surgical trajectory, e.g. like shown in one of the FIGS. 5, 6 and 7.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A method of visualizing a surgical trajectory, the method comprising:
   receiving 3D imaging information of a region to undergo surgery;
   combining the received 3D imaging information with data from an anatomic model repository to obtain a combined map of the region to undergo surgery, the combined map comprising expected positions of anatomical structures in the region to undergo surgery;
   receiving the surgical trajectory for the surgery;
   determining positions of intersections of the surgical trajectory with the anatomical structures; and
   providing the positions of the intersections in a coordinate system aligned with the surgical trajectory.

2. A method of visualizing a surgical trajectory as claimed in claim 1, wherein the combined map includes a statistical map of the region to undergo surgery, the statistical map including probabilities of a presence of the anatomical structures at positions in the region.

3. A method of visualizing a surgical trajectory as claimed in claim 1, further comprising:
   displaying the positions of the intersections in the coordinate system aligned with the surgical trajectory.

4. A method of visualizing a surgical trajectory as claimed in claim 1, wherein the positions of the intersections are provided as a distance between the intersections and a target of the surgical trajectory.

5. A method of visualizing a surgical trajectory as claimed in claim 1, wherein the surgical trajectory is a planned surgical trajectory.

6. A method of visualizing a surgical trajectory as claimed in claim 1, wherein a current position of a surgical tool is mapped on the coordinate system aligned with the surgical trajectory.

7. A method of visualizing a surgical trajectory as claimed in claim 6, wherein the surgical tool is an electrophysiological probe, the method further comprising:
   receiving electrophysiological signals-from the probe; and
   visualizing the electrophysiological signals at the related positions in the coordinate system.

8. A method of visualizing a surgical trajectory as claimed in claim 6, wherein the surgical tool is a needle probe with an integrated optical fiber for reflectance measurements, the method further comprising:
   acquiring optical spectra from the reflectance measurements from the probe; and
   visualizing the optical spectra at the related positions in the coordinate system.

9. A method of visualizing a surgical trajectory as claimed in claim 6, wherein the surgical tool is an electrophysiological probe, the method further comprising:
   receiving electrophysiological signals from the probe;
   extracting features from the received electrophysiological signals;
   relating the extracted features to positions in the coordinate system; and
   visualizing the extracted features in combination with the related positions in the coordinate system.

10. A method of visualizing a surgical trajectory as claimed in claim 9, wherein the electrophysiological probe is a neuro-electrophysiological probe.

11. A method of visualizing a surgical trajectory as claimed in claim 6, wherein the surgical trajectory includes at least part of a path traveled by the surgical tool towards the current position.

12. A method of visualizing a surgical trajectory as claimed in claim 6, wherein the surgical trajectory includes at least part of an expected path to be traveled by the surgical tool from the current position.

13. A method of visualizing a surgical trajectory as claimed in claim 1, wherein the 3D imaging information includes MRI or CT scan images.

14. A computer program product embodied on a non-transitory computer-readable medium, which program is operative to cause a processor to perform the method of claim 1.

15. A system for visualizing a surgical trajectory, the system comprising:
   an input for receiving 3D imaging information of a region to undergo surgery and the surgical trajectory for the surgery;
   a memory for storing the received 3D imaging information, the surgical trajectory and an anatomic model repository;
   a processor being operative to:
      combine the 3D imaging information with data from the anatomic model repository to obtain a combined map of the region to undergo surgery, the combined map comprising expected positions of anatomical structures in the region to undergo surgery, and
      determine positions of intersections of the at least one surgical trajectory with the anatomical structures; and
   an output for providing the positions of the intersections in a coordinate system aligned with the surgical trajectory.

16. A method of visualizing a surgical trajectory as claimed in claim 1, wherein the combined map and the surgical trajectory is used for determining positions of intersections of the surgical trajectory with the anatomical structures.

17. A system of visualizing a surgical trajectory as claimed in claim 15, wherein the processor uses the combined map and the surgical trajectory to determine positions of intersections of the surgical trajectory with the anatomical structures.

* * * * *